United States Patent [19]

Falling

[11] Patent Number: 5,117,013
[45] Date of Patent: May 26, 1992

[54] PROCESS FOR THE SELECTIVE HYDROGENATION γ, δ-EPOXYALKENES TO EPOXYALKANES

[75] Inventor: Stephen N. Falling, Kingsport, Tenn.

[73] Assignee: Eastman Kodak Company, Rochester, N.Y.

[21] Appl. No.: 728,466

[22] Filed: Jul. 11, 1991

Related U.S. Application Data

[62] Division of Ser. No. 518,629, May 3, 1990, Pat. No. 5,077,418.

[51] Int. Cl.$^5$ .......................................... C07D 301/02
[52] U.S. Cl. ................................. 549/540; 568/700; 568/840
[58] Field of Search ................. 549/540; 568/700, 840

[56] References Cited

U.S. PATENT DOCUMENTS 2,561,984  7/1951  Hillyer et al. ...................... 260/598

FOREIGN PATENT DOCUMENTS 49-20173  5/1974  Japan .

OTHER PUBLICATIONS

Rylander, "Catalytic Hydrogenation Over Platinum Metal", Academic Press, New York, p. 478, 1967.
J. Am. Chem. Soc., 80, 4341 (1958).
Zh. Obshch. Khim., 28, 3046 and 3051 (1958).
J. Am. Chem. Soc., 83, 3096 (1961).

*Primary Examiner*—C. Warren Ivy
*Assistant Examiner*—Ba K. Trinh
*Attorney, Agent, or Firm*—J. Frederick Thomsen; William P. Heath, Jr.

[57] ABSTRACT

Disclosed is a novel process for the preparation of epoxyalkanes and epoxycycloalkanes which comprises hydrogenating γ,δ-epoxyalkenes or γ,δ-epoxycycloalkenes in the presence of a rhodium catalyst. The process is especially useful for the preparation of 1,2-epoxybutane from 3,4-epoxy-1-butene.

1 Claim, No Drawings

PROCESS FOR THE SELECTIVE HYDROGENATION γ, δ-EPOXYALKENES TO EPOXYALKANES

This is a divisional application of application Ser. No. 07/518,629 filed on May 3, 1990, now U.S. Pat. No. 5,077,418.

This invention pertains to a novel process for the conversion of γ,δ-epoxyalkenes and γ,δ-epoxycycloalkenes to the corresponding epoxyalkanes and epoxycycloalkanes. More specifically, this invention pertains to the catalytic hydrogenation of γ,δ-epoxyalkenes and γ,δ-epoxycycloalkenes by means of a rhodium catalyst whereby the olefinic unsaturation is hydrogenated without significant hydrogenolysis of the conjugated epoxy group.

U.S. Pat. No. 4,897,498 describes an efficient process for the preparation of γ,δ-epoxyalkenes by the selective monoepoxidation of dienes, e.g., 3,4-epoxy-1-butene from butadiene. A valuable compound which may be obtained from 3,4-epoxy-1-butene is 1,2-epoxybutane, also referred to in the literature as 1,2-butylene oxide or butylene oxide.

According to Rylander, Catalytic Hydrogenation Over Platinum Metals, Academic Press, New York, page 478 (1967), epoxides, with a few exceptions (Berson and Suzuki, J. Am. Chem. Soc., 80, 4341 [958]), readily undergo hydrogenolysis over platinum metal catalysts and the major product is usually an alcohol or mixture of alcohols resulting from cleavage of a carbon-oxygen bond; other products may arise by cleavage of the carbon-carbon bond and by loss of the oxygen function.

The catalytic hydrogenation of 3,4-epoxy-1-butene to butyraldehyde over palladium and to 1-butanol over Raney nickel is described in U.S. Pat. No. 2,561,984. No mention is made of the use of rhodium catalysts nor the observation of 1,2-epoxybutane formation. The hydrogenation of 3,4-epoxy-1-butene also has been reported by Russian workers in Zh. Obshch. Khim., 28, 3046 and 3051 (1958). They hydrogenated 3,4-epoxy-1-butene in methanol or ethanol with platinum, palladium, and Raney nickel catalysts to give 1-butanol. They state that crotyl alcohol was the principal intermediate in the reduction, although butyraldehyde was also observed. Selective double bond hydrogenation was not observed in any example.

Rhodium has been reported (J. Am. Chem. Soc., 83, 3096 [1961]) to be effective for a double bond reduction in the presence of an epoxide group in a fumagillin derivative. In this literature example, however, the epoxide is trisubstituted and less prone to hydrogenolysis due to stearic hindrance. Additionally the double bond and epoxide were not conjugated as they are in 3,4-epoxy-1-butene. By the term "conjugated" is meant that the carbon-carbon double bond and the epoxide group are adjacent, or stated another way, the epoxide oxygen is attached to the allylic carbon atom.

The significance of the conjugated γ,δ-epoxyalkene system existing in 3,4-epoxy-1-butene is demonstrated by Raney nickel-catalyzed hydrogenations of 3,4-epoxy-1-butene and 1,2-epoxy-7-octene under mild conditions of 50° C. and 3.5 bars total pressure. The hydrogenation of 3,4-epoxy-1-butene gives 40.5% 1,2-epoxybutane and 58.4% 1-butanol whereas the hydrogenation of 1,2-epoxy-7-octene, wherein the double bond and epoxy group are separated by 4 carbon atoms, gives 94.4% 1,2-epoxyoctane.

I have discovered that γ,δ-epoxyalkenes and γ,δ-epoxycycloalkenes may be selectively hydrogenated in the presence of a rhodium catalyst whereby the olefinic unsaturation is hydrogenated without significant hydrogenolysis of the conjugated epoxy group. The present invention therefore includes a process for the preparation of epoxyalkanes and epoxycycloalkanes by hydrogenating γ,δ-epoxyalkenes and γ,δ-epoxycycloalkenes in the presence of a rhodium catalyst. A second embodiment of my invention comprises the steps of (1) hydrogenating γ,δ-epoxyalkenes and γ,δ-epoxycycloalkenes in the presence of a rhodium catalyst to obtain a mixture comprising (a) an epoxyalkane containing a minor amount of an aldehyde or (b) an epoxycycloalkane containing a minor amount of a ketone; and (2) hydrogenating the mixture in the presence of a nickel catalyst to convert the aldehyde or ketone to the corresponding alcohol.

The γ,δ-epoxyalkene and γ,δ-epoxycycloalkene reactants may contain from 4 to about 20 carbon atoms, preferably from 4 to about 8 carbon atoms. Examples of the epoxyalkene and epoxycycloalkene reactants include compounds having the structural formula:

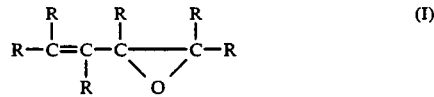

wherein each R is independently selected from hydrogen, alkyl of up to about 8 carbon atoms, a carbocyclic or heterocyclic aryl group of about 5 to 10 carbon atoms or halogen or any two R substituents collectively may represent an alkylene group forming a ring, e.g., alkylene containing in the main chain 4 to about 6 carbon atoms. The preferred epoxyalkene reactants comprise compounds of formula (I) wherein the R substituents individually represent hydrogen, lower alkyl, e g., alkyl of up to about 4 carbon atoms, or halogen or collectively represent straight or branched chain alkylene of 4 to about 8 carbon atoms, especially compounds of formula (I) wherein at least 4 of the R groups represent hydrogen. Exemplary compounds contemplated for use in the practice of the present invention include 3,4-epoxy-3-methyl-1-butene, 2,3-dimethyl-3,4-epoxy-1-butene, 1,3-cyclooctadiene monoepoxide, 3,4-epoxy-1-butene, and the like. The epoxyalkene reactant of primary interest is 3,4-epoxy-1-butene.

The epoxyalkane and epoxycycloalkane compounds produced in accordance with the present invention have the formula

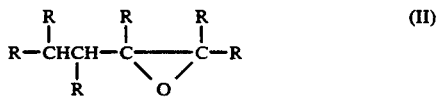

wherein the R substituents are defined above. These compounds are useful in the manufacture of polyethers, alkylene and cycloalkylene glycols, aminoalkanols and aminocycloalkanols, epoxy resins, urethane polyols, nonionic surfactants and stabilizers for chlorinated hydrocarbons.

The rhodium catalyst which may be employed in the process include rhodium and rhodium compounds reducible to rhodium, e.g., Rh$_2$O$_3$, under the process conditions. The catalyst preferably is a supported rhodium catalyst e.g., a catalyst comprised of about 0.1 to 20.0 weight percent, preferably, 0.1 to 10 weight percent, rhodium, based on the total weight of the catalyst, deposited on the surface of a suitable catalyst support material. Typical catalyst supports include carbon, alumina, silica, titania, kieselguhr, molecular sieves and zeolites. A particularly useful catalyst comprises about 0.5 to 5.0 weight percent rhodium on carbon.

The hydrogenation conditions of temperature and pressure can vary substantially depending on several factors such as contact time with the rhodium catalyst, the amount of catalyst, the amount of rhodium present on the support and the mode of operation. Hydrogenation temperatures of about 20° to 150° C. may be used although milder temperatures in the range of about 25° to 80° C. are advantageous to maximize conversion to the desired epoxyalkane or epoxycycloalkane and minimize conversion to alcohols and aldehydes. The hydrogenation process may be carried out using total pressures in the range of about 2 to 345 bars, preferably about 2 to 56 bars. The process pressures are set forth herein in bars gauge, i.e., bars pressure above atmospheric or ambient pressure. As noted above, the optimum combination of temperature and pressure depends on other process variables but can be readily ascertained by those skilled in the art.

The process of this invention optionally may be carried out in the presence of an inert, organic solvent. Examples of such solvents include aliphatic and aromatic hydrocarbons such as heptane, toluene, xylene and mixed xylene isomers, alkanols such as ethanol, and ethers such as tetrahydrofuran. The process may be carried out in a batch, semi-continuous or continuous mode of operation. For example, batch operation may comprise agitating a slurry of a rhodium catalyst in a γ,δ-epoxyalkene or γ,δ-epoxycycloalkene and, optionally, a solvent in a pressure vessel for a time sufficient to convert essentially all of the unsaturated epoxide to other compounds. The catalyst can be separated from the hydrogenated mixture by filtration and the components of the filtrate separated by distillation.

A preferred mode of operations uses a fixed bed of a supported rhodium catalyst wherein a γ,δ-epoxyalkene or γ,δ-epoxycycloalkene is hydrogenated in the gas or, especially, liquid phase, optionally in the presence of an inert diluent or solvent. Liquid phase operation typically involves feeding a solution of the unsaturated epoxide in an inert solvent-diluent to the top of a columnar, pressure reactor containing one or more fixed beds of a supported rhodium catalyst. The reactant solution flows (trickles) over the catalyst bed in the presence of hydrogen at elevated temperature and pressure and the hydrogenated product exits the bottom of the reactor and is separated into its components by distillation. The feed rates employed in liquid phase operation may be in the range of about 0.01 to 100 liquid hour space velocities (LHSV, unit volume of feed per unit volume of catalyst). Under most conditions, the LHSV will be in the range of about 0.1 to 10.

When hydrogenating 3,4-epoxy-1-butene, any 1-butanol (bp 117° C.) produced is readily separated from the epoxybutane product (bp 63° C.) by distillation. However, any butyraldehyde (bp 75° C.) present is difficult to remove from the desired product. Thus, in a preferred mode of operation, the initial crude product obtained from the hydrogenation process described hereinabove is subjected to a second hydrogenation under mild conditions using a nickel catalyst, e.g., Raney nickel or a supported nickel catalyst. This ancillary, nickel-catalyzed hydrogenation converts any butyraldehyde present to 1-butanol without significant conversion of the 1,2-epoxybutane.

In the second embodiment of my invention, a γ,δ-epoxyalkene or γ,δ-epoxycycloalkene is first hydrogenated in the presence of a rhodium catalyst as described hereinabove to obtain a mixture comprising (a) an epoxyalkane containing a minor amount of an aldehyde or (b) an epoxycycloalkane containing a minor amount of a ketone. The aldehyde or ketone may comprise up to about 25 weight percent of the total weight of the epoxyalkane or epoxycycloalkane and the aldehyde or ketone. In the second step, the mixture is hydrogenated in the presence of a nickel catalyst to convert the aldehyde or ketone to the corresponding alcohol which may be separated from the epoxyalkane or epoxycycloalkane according to conventional distillation procedures. The nickel catalyst may be Raney nickel or a catalyst consisting of nickel on a support material. The hydrogenation conditions of temperature and pressure are in the range of about 20° to 150° C. and 2 to 345 bar although temperatures in the range of about 25° to 80° C. and pressures in the range of about 2 to 56 bar are more typical.

The process provided by the present invention is further illustrated by the following examples. Gas chromatographic (GC) analyses are reported in area-percent and were performed on a Hewlett-Packard 5890A gas chromatograph with a DB5-30W capillary column; temperature program 35° C. (4.5 min), 20° C./min to 240° C. (hold 2 minutes). $^1$H NMR analyses were performed on a Varian Gemini 300 spectrometer (300 MHz) using CDCl$_3$ as solvent and tetramethylsilane as internal standard.

EXAMPLE 1

To a nitrogen-purged glass autoclave liner was charged 1.00 g of 5% rhodium on carbon (Engelhard), 80 mL of p-xylene, 40.0 g (0.571 mole) of 3,4-epoxy-1-butene), and a Teflon-coated magnetic stirring bar. Then the liner was stoppered and the mixture was hydrogenated in a magnetically-stirred autoclave at 40°–50° C. and 20.7 bar (300 psig) for 7.3 hours (hydrogen uptake complete after six hours). GC analysis of the crude mixture showed (disregarding solvent): 0.70% low boilers, 90.52% 1,2-epoxybutane/butyraldehyde, 8.41% 1-butanol, and 0.07% crotonaldehyde. The mixture was fractionally distilled to give: fraction 1, 58°–61° C., 2.34 g, 95.7% 1,2-epoxybutane/butyraldehyde, 4.3% low boilers; and fraction 2, 61°–65° C., 30.87 g, 99.70% 1,2-epoxybutane/butyraldehyde. NMR of fraction 2 showed a 1,2-epoxybutane/butyraldehyde mole-ratio of 95.3/4.7. Weight yield of fraction 2 was 75.16% (theory 41.07 g).

EXAMPLE 2

To a nitrogen-purged, 250-mL, Parr pressure bottle was charged 0.50 g of 5% rhodium on carbon (Engelhard), 50 mL of tetrahydrofuran, and 14.0 g (0.200 mole) of 3,4-epoxy-1-butene. The bottle was placed in a Parr, shaker-type hydrogenation apparatus, purged three times with nitrogen then two times with hydrogen. The bottle was pressurized to 3.5 bar (50 psig) with hydrogen and agitation begun. The mixture was heated to 50° C. After 4 hours hydrogen uptake was complete.

NMR and GC analysis of this mixture showed (disregarding solvent): 84.7% 1,2-epoxybutane, 2.7% butyraldehyde, 0.9% crotonaldehyde, 6.5% 1-butanol, and 4.1% 2.buten-1-ol.

EXAMPLES 3-14

Using the procedure described in Example 2, 3,4-epoxy-1-butene was hydrogenated to 1,2-epoxybutane using various hydrogenation conditions and solvents except in Example 7 wherein no solvent was employed. The catalysts used were:

Examples 3 and 4—5% rhodium on alumina
Examples 5-13—5% rhodium on carbon
Example 14—rhodium oxide ($Rh_2O_3 \cdot xH_2O$)

The composition of the mixtures hydrogenated are set forth in Table I wherein pressure (Press) is given in bars gauge, temperature (Temp) is given in ° C. and time is the period of hydrogenation in hours. The amounts of catalysts (Cat) and 3,4-epoxy-1-butene (EpB) are given in grams and the amount of solvent is given in mL. The composition of the hydrogenated mixtures (excluding solvent) obtained in each of Examples 3-14 are reported in Table II wherein EpB is the area percent of unreacted 3,4-epoxy-1-butene, BO is the area percent of the desired 1,2-epoxybutane and nPrCHO, Crot, nBuOH and Butenols refers to the area percents of n-butyraldehyde, crotonaldehyde, n-butanol and butanol (combined 2- and 3-buten-1-ol) present in the hydrogenated mixtures.

TABLE I

| Example | Amounts of Cat | Amounts of EpB | Solvent/Amount | Press | Temp | Time |
|---|---|---|---|---|---|---|
| 3 | 0.25 | 14.0 | Tetrahydrofuran/50 | 3.5 | 50 | 20.0 |
| 4 | 1.07 | 33.6 | Mixed xylenes/75 | 3.5 | 40-60 | 7.0 |
| 5 | 0.40 | 15.0 | Ethanol/30 | 3.5 | 40 | 16.0 |
| 6 | 1.00 | 34.6 | Heptane/65 | 3.5 | 40 | 9.0 |
| 7 | 1.00 | 31.4 | None | 3.5 | 40 | 6.0 |
| 8 | 2.00 | 70.3 | p-Xylene/130 | 3.5 | 40 | 22.0 |
| 9 | 0.40 | 15.1 | p-Xylene/30 | 3.5 | 40 | 10.0 |
| 10 | 0.50 | 14.9 | Toluene/50 | 3.5 | 50 | 6.0 |
| 11 | 1.75 | 70.6 | Mixed xylenes/150 | 3.5 | 30 | 22.0 |
| 12 | 1.56 | 55.7 | Mixed xylenes/140 | 3.5 | 40 | 11.0 |
| 13 | 2.00 | 70.4 | Mixed xylenes/150 | 3.5 | 50 | 10.0 |
| 14 | 0.052 | 13.1 | p-Xylene/50 | 3.6 | 55 | 17.0 |

TABLE II

| Example | EpB | BO | nPrCHO | Crot | nBuOH | Butenols |
|---|---|---|---|---|---|---|
| 3 | 0.0 | 88.9 | Trace | 0.7 | 6.4 | 3.2 |
| 4 | 0.0 | 54.8 | 7.0 | 7.4 | 18.4 | 9.2 |
| 5 | 5.5 | 75.1 | Trace | 0.7 | 4.6 | 12.1 |
| 6 | 0.0 | 84.0 | 4.4 | 0.7 | 7.8 | 2.6 |
| 7 | 0.0 | 86.5 | 4.6 | 0.7 | 5.0 | 2.4 |
| 8 | 0.0 | 90.8 | Trace | 0.7 | 5.9 | 2.0 |
| 9 | 0.0 | 89.8 | Trace | 0.8 | 5.1 | 2.4 |
| 10 | 0.0 | 84.7 | Trace | 1.4 | 7.5 | 3.6 |
| 11 | 0.0 | 93.2 | 0.0 | 0.5 | 5.0 | 1.9 |
| 12 | 0.0 | 90.5 | Trace | 0.2 | 5.7 | 2.3 |
| 13 | 0.0 | 87.8 | Trace | 0.3 | 6.6 | 3.3 |
| 14 | 0.0 | 59.6 | 16.9 | Trace | 16.8 | 0.0 |

EXAMPLE 15

This example describes the nickel-catalyzed hydrogenation of a mixture consisting of 95.3 weight percent 1,2-epoxybutane and 4.7 weight percent butyraldehyde to convert the butyraldehyde to the readily-separable 1-butanol.

To a nitrogen-purged, 250-mL, Parr pressure bottle was charged 1.15 g of water-wet Raney nickel. The catalyst was rinsed three times with a small amount of tetrahydrofuran then three times with a small amount of p-xylene. To the bottle was added 80 mL of p-xylene, 30.32 g (0.4205 mole) of 1,2-epoxybutane and 1.51 g (0.209 mole) of n-butyraldehyde. The bottle was placed in a Parr, shaker-type hydrogenation apparatus, purged three times with nitrogen then two times with hydrogen. The bottle was pressurized to 3.5 bars with hydrogen and agitation begun. The mixture was then heated to 45° C. Little hydrogen uptake was observed during the hydrogenation (2.5 hours at 3.4-3.5 bars). NMR and GC analysis of the crude mixture showed (disregarding solvent): 95.13% 1,2-epoxybutane, 0% butyraldehyde, and 3.77% 1-butanol. The mixture was fractionally distilled to give fraction 1, bp 45°-61° C., 1.37 g, 98.61% 1,2-epoxybutane, 0.18% tetrahydrofuran, 0.055% 1-butanol, 0.79% p-xylene; fraction 2, bp 61°-63° C., 19.21 g, 98.59% 1,2-epoxybutane, 0.22% tetrahydrofuran, 0.12% 1-butanol, 1.01% p-xylene; fraction 3, bp 63° C., 4.97 g, 97.83% 1,2-epoxybutane, 0.28% tetrahydrofuran, 0.35% 1-butanol, 1.45% p-xylene; fraction 4, bp 63°-81° C., 3.31 g, 82.55% 1,2-epoxybutane, 0.38% tetrahydrofuran, 5.48% 1-butanol, 1.29% p-xylene. Fractions 1, 2, and 3 were combined to give 25.55 g of product. NMR and GC analysis of the combined fraction showed 98.39% 1,2-epoxybutane, 0% butyraldehyde, 0.204% tetrahydrofuran, 0.155% 1-butanol, 1.069% p-xylene. The weight of product on a 100% basis was 25.14 g (82.9% recovery).

EXAMPLE 16

To a nitrogen-purged, 250-mL, Parr pressure bottle was charged 0.20 g of 5% palladium on carbon (Engelhard), 40 mL of toluene, and 1.87 g (0.0147 mole) of 1,3-cyclooctadiene monoepoxide (95.6% pure). The bottle was placed in a Parr, shaker-type hydrogenation apparatus, purged three times with nitrogen then two times with hydrogen. The bottle was pressurized to 3.5 bars with hydrogen and agitation begun. The mixture was heated to 52° C. After 3 hours hydrogen uptake was complete. The solvent was removed by rotary evaporation to give 1.72 g of cyclooctene oxide, assay 96.7% (theory 1.82 g, 91.4% assay yield).

COMPARATIVE EXAMPLE 1

To a nitrogen-purged, 250-mL, Parr pressure bottle was charged 0.25 g of 5% palladium on carbon (Engelhard), 50 mL of tetrahydrofuran, and 15.7 g (0.224 mole) of 3,4-epoxy-1-butene. The bottle was placed in a Parr, shaker-type hydrogenation apparatus, purged three times with nitrogen then two times with hydrogen. The bottle was pressurized to 3.5 bars with hydrogen and agitation begun. The temperature rapidly rose to 55° C. due to heat of reaction and was held at 50°-55° C. for three hours at which time hydrogen uptake was complete. NMR and GC analysis of the crude mixture showed (disregarding solvent): 27.0% 1,2-epoxybutane, 54.8% butyraldehyde, 9.1% 1-butanol.

COMPARATIVE EXAMPLE 2

This example shows that palladium catalyzes the hydrogenation of a non-conjugated epoxyalkene to the corresponding epoxyalkane whereas, as shown by Comparative Example 1, the product of the palladium-catalyzed hydrogenation of a conjugated epoxyalkene (3,4-epoxy-1-butene) consists of a major proportion of butyraldehyde.

To a nitrogen-purged, 250.mL, Parr pressure bottle was charged 0.20 g of 5% palladium on carbon, 50 mL of tetrahydrofuran, and 12.6 g (0.0901 mole) of 1,2.epoxyoct-7-ene (90.2% pure). The bottle was placed in a Parr, shaker-type hydrogenation apparatus, purged three times with nitrogen then two times with hydrogen. The bottle was pressurized to 3.5 bars with hydrogen and agitation begun. The temperature rapidly rose from 29° C. to 54° C. due to heat of reaction. After 20 minutes hydrogen uptake was complete but hydrogenation was continued for two hours at 45°–50° C. and 2.8 bars. NMR and GC analysis of the reaction mixture showed complete reduction of the double bond without loss of the epoxide function (no octanal, 1- or 2-octanol observed). The solvent was removed by rotary evaporation to give 12.4 g of product as a colorless liquid, assay 82.9% (theory 1.6 g, 92.2% assay yield).

COMPARATIVE EXAMPLES 3–8

Additional experiments were performed wherein 3,4-epoxy-1-butene was hydrogenated in the presence of other Group VIII noble metal catalysts:

1% Platinum on alumina—Comparative Examples 3 and 4

Platinum on carbon—Comparative Example 5

Palladium on alumina—Comparative Examples 6 and 7

Platinum oxide—Comparative Example 8

Comparative Examples 3, 6 and 8 were carried out an initial pressure of 3.5 bar gauge according to the procedure described in Comparative Example 1. Comparative Examples 4, 5 and 7 were carried out at 20.7 bar gauge according to the procedure of Example 1. The mixtures hydrogenated and the results obtained are shown in Tables III and IV.

TABLE III

| Example | Amounts of Cat | Amounts of EpB | Solvent/Amount | Press | Temp | Time |
|---|---|---|---|---|---|---|
| C-3 | 0.50 | 14.1 | Tetrahydrofuran/35 | 3.5 | 50 | 7.0 |
| C-4 | 0.75 | 14.2 | Tetrahydrofuran/35 | 20.7 | 100 | 4.6 |
| C-5 | 0.75 | 14.2 | Tetrahydrofuran/35 | 20.7 | 100 | 4.3 |
| C-6 | 0.25 | 15.5 | Tetrahydrofuran/50 | 3.5 | 25–55 | 6.0 |
| C-7 | 0.13 | 15.4 | Tetrahydrofuran/35 | 20.7 | 100 | 4.0 |
| C-8 | 0.14 | 14.1 | Tetrahydrofuran/42 | 3.5 | 50 | 20.0 |

TABLE IV

| Example | EpB | BO | nPrCHO | Crot | nBuOH | Butenols |
|---|---|---|---|---|---|---|
| C-3 | 4.0 | 33.0 | 12.3 | 2.9 | 22.0 | 16.1 |
| C-4 | 0.0 | 39.9 | 2.7 | 5.4 | 23.4 | 23.7 |
| C-5 | 6.4 | 19.0 | 6.3 | 2.0 | 21.4 | 26.9 |
| C-6 | 0.0 | Trace | 86.9 | 0.0 | 7.4 | 0.0 |
| C-7 | 0.0 | Trace | 78.4 | 0.0 | 12.7 | 0.0 |
| C-8 | 0.0 | 22.0 | 5.4 | 0.0 | 56.0 | 9.4 |

The invention has been described in detail with particular reference to preferred embodiments thereof, but it will be understood that variations and modifications can be effected within the spirit and scope of the invention.

I claim:

1. A process for the preparation of 1,2epoxybutane which comprises the steps of:
   (1) hydrogenating 3,4-epoxy-1-butene in the presence of a supported rhodium catalyst at a pressure of about 2 to 56 bar and a temperature of about 25° to 80° C. to obtain a mixture of 1,2-epoxybutane and butyraldehyde;
   (2) hydrogenating the mixture obtained from step (1) in the presence of a nickel catalyst to convert the butyraldehyde to butanol;
   (3) separating the 1,2-epoxybutane from the 1-butanol.

* * * * *